United States Patent [19]

Kraus

[11] 4,237,057

[45] Dec. 2, 1980

[54] SYNTHESIS OF QUINONE PYRANO-GAMMA-LACTONE ANTIBIOTICS AND ANTIFUNGAL AGENTS

[75] Inventor: George A. Kraus, Ames, Iowa

[73] Assignee: Iowa State University Research Foundation, Inc., Ames, Iowa

[21] Appl. No.: 42,314

[22] Filed: May 25, 1979

[51] Int. Cl.$^3$ .................................... C07D 493/04
[52] U.S. Cl. .................... 260/343.3 R; 260/347.8
[58] Field of Search ............... 260/343.3 R, 347.4, 260/347.8

[56] References Cited

PUBLICATIONS

Omura et al. Jour. Chem. Soc. Chem. Comm. pp. 320–321, 1976.
Bergy The Journ. of Antibiotics 21, Jul. 1969, pp. 454–457.

Primary Examiner—Henry R. Jiles
Assistant Examiner—Jane T. Fan
Attorney, Agent, or Firm—Zarley, McKee, Thomte, Voorhees & Sease

[57] ABSTRACT

An efficient synthesis of quinone pyrano-gamma-lactone antibiotics such as kalafungin and the new compound 9-deoxykalafungin in four basic steps from readily available starting materials. The key step in which all of the carbon atoms present in the target molecule are assembled is the addition of an alkoxy furan to a two position functionally substituted 1,4 naphthoquinone. This is followed by alkylating to provide protecting groups, hydride reduction, removal of the protecting groups, internal cyclization and by oxidative dealkylation to provide practical overall yields of the desired antibiotics.

10 Claims, No Drawings

SYNTHESIS OF QUINONE PYRANO-GAMMA-LACTONE ANTIBIOTICS AND ANTIFUNGAL AGENTS

GRANT REFERENCE

The invention described herein was made in the course of work under a grant or award from the Department of Health, Education and Welfare.

BACKGROUND OF THE INVENTION

Kalafungin, grantican B and the nanaomycins are members of a growing family of naturally occurring antibiotics containing quinones fused to a pyrano-gamma-lactone moiety. Clinical testing has shown kalafungin to be inhibitory in vitro against a variety of pathogenic fungi, yeasts, protozoa and gram positive and gram negative bacteria. To date, no synthetic approaches to this interesting class of natural products have appeared.

This invention has as its primary objective an overall synthesis route for this class of antibiotic compounds. In addition, a new and novel antibiotic compound, which is not naturally occurring, 9-deoxykalafungin, has been prepared. And tests show this compound to exhibit, in some instances, superiority in terms of inhibitory effect when compared to naturally occurring kalafungin.

Accordingly, one object of the invention is to prepare via synthetic approaches, an interesting class of natural products by construction of the basic ring system of the quinone pyrano-gamma-lactone antibiotics in a short, efficient synthesis route.

Yet another object of this invention is to prepare such compounds as mentioned above at yield levels which are economically feasible for mass production.

A still further object is to prepare 9-Deoxykalafungin.

The method and manner of accomplishing each of these stated objectives will become apparent from the detailed description of the invention which follows.

SUMMARY OF THE INVENTION

A method of preparing quinone pyrano-gamma-lactone antibiotics such as kalafungin and 9-deoxykalafungin, which comprises reacting, under anhydrous conditions, a two position functionally substituted 1,4 naphthoquinone with an alkoxy furan, to provide a first synthesis intermediate having the carbon skeleton structure of the antibiotic. Thereafter, an alkylating agent is added to the synthesis intermediate to protect the 1,4 position keto groups, the functional groups of the two position substituted moiety are reduced to alcoholic groups, and after the reduction which is preferably a hydride reduction, a deblocking agent and a cyclization agent are added to provide removal of the alkyl portion of the alkoxy group and to provide ring formation between the alcoholic group of said two position substituent and said furan ring, and finally oxidative dealkylating of the 1,4 positions occurs to provide a quinone pyrano-gamma-lactone antibiotic, such as kalafungin or 9-deoxykalafungin.

DETAILED DESCRIPTION OF THE INVENTION

As heretofore mentioned, kalafungin is a known antibiotic. It is an effective anti-fungal agent. Heretofore it has been prepared via a fermentation broth of the microorganism *Streptomyces tananshunsis*. Such fermentation processes are, of course, expensive, time consuming and provide poor overall yields. For further details with regard to such processing for kalafungin, see Johnson and Dietz, Appl., *Microbiology*, 16, 1815 (1968), which is incorporated herein by reference.

Kalafungin, grantican B, nanaomycins and deoxykalafungin all have in common a basic naphthoquinone pyrano ring, the official name of which is 1-H Naptho [2,3-c] pyran 5,10 dione. The basic discovery of this invention involves synthesis of this ring structure, with, of course, substituted moieties which may be added to the basic ring structure for synthesis of any particular quinone pyrano-gamma-lactone antibiotic. Heretofore, there has been no successful synthesis route for preparation of these type of compounds.

In the first step of the synthesis, a two position functionally substituted 1,4 naphthoquinone having the formula:

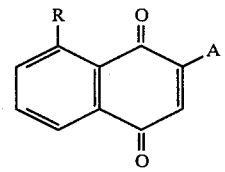

is reacted with an alkoxy furan having the formula:

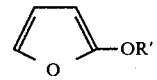

With respect to the naphthoquinone, R* may be a lower alkyl group, hydrogen, an alkoxy group or hydroxyl as well as chloride. A precise moiety represented by R is not critical and is merely selected dependent upon the ultimate antibiotic compound being prepared. For example, when kalafungin is prepared, R represents OH, and when deoxykalafungin is prepared, R represents hydrogen. Similarly, if grantican B is being prepared, or the nanaomycins R represents a hydroxyl group.

"A" can be virtually any moiety which in subsequent processing steps can be reduced to an alcoholic functional group for use during the cyclization step. For example, it can be lower keto groups, ester groups, aldehyde groups or a nitrile group. In preparing kalafungin and deoxykalafungin, it is most preferred that "A" be a keto group. Specifically for these two mentioned compounds, it is most preferred that "A" be an acetyl group, that is —CH$_3$C0. Generally, it is preferred that A be a keto group of C$_1$ to C$_{10}$ chain length.

Turning now to the alkoxy furan reaction ingredient, R' may be any moiety which is easily removable with dilute acid. That is, any acid labile group has been found satisfactory. For most purposes, and therefore preferred with respect to the process of this invention, R' can be tertiary butyl or tertiarybutyldimethylsiloxy moieties. Both of these are preferred because they are easily removable by dilute acid in subsequent processing steps. However, it should be understood that R' may also be other lower acid labile groups such as methoxymethyl.

The initial reaction between the naphthoquinone reactant and the alkoxy furan must be conducted under anhydrous conditions because water would react with the quinone structure. Similarly, the presence of other solvents which have hydroxyl groups must be avoided for the same reason. For these reasons, it is desirable to conduct the reaction in an inert atmosphere, preferably a nitrogen atmosphere, and in the presence of a solvent such as toluene, benzene, tetrahydrofuran, methylene chloride, chloroform, ether, or the like. These solvents can all be described as organic aprotic solvents. All of them have in common the fact that they will dissolve the alkylating agent which is subsequently added as hereinafter explained.

The reaction temperature does not appear to be a critical factor, and the reaction may be run at temperatures of from −78° C. to 0° C. and even up to room temperature. The reaction seems to go to completion rather quickly and so reaction time is not a factor. Generally, however, four to eight hours assures substantially complete reaction.

In every instance, unless hereinafter specified to the contrary, it is preferred for overall reaction synthesis efficiency that the amount of ingredients be reaction equivalent amounts. It should, however, be understood that more or less may be employed if desired, but for overall process efficiencies, since the reactions are generally addition reactions, equivalent amounts are most desirable.

The addition of the naphthoquinone and the alkoxy furan, provides the following addition structure which forms the basic carbon skeleton of the desired antibiotics.

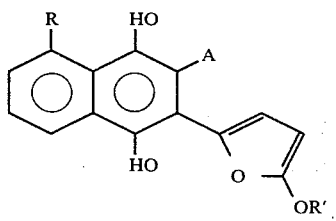

Simultaneously with the formation of this first synthesis intermediate, the product is alkylated in the presence of a base to protect the 1,4 position keto groups of said naphthoquinone. This alkylation is a well known procedure and need not be described with great particularity herein. It can generally be described as a Williamson-ether synthesis. The purpose of the alkylating agent is to protect the quinone dione groups by adding protective blocking groups thereto, thus preserving the desired structure.

The alkylation must be conducted under basic conditions in order for it to go and generally this can be accomplished by conducting the reaction in the presence of sodium carbonate or potassium carbonate. The addition of base is important, as hereinafter explained, in order to make sure that the product is tautomerized to the hydroquinone derivative, synthesis intermediate.

The amount of base can be from 2 to 4 equivalents.

The Williamson-ether alkylation can be conveniently accomplished by solvent removal and then adding directly to the reaction vessel for the first step herein described, a suitable alkylating agent such as dimethyl sulfate, while refluxing with anhydrous acetone. The result is formation of a second synthesis intermediate with the methylating protective groups having the following formula:

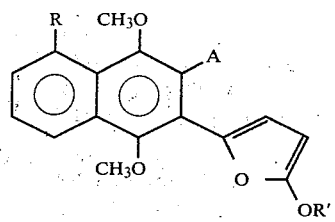

Summarizing for a moment, it can be seen that in the overall basic reaction step herein described as the "first step", in fact there are three separate reactions which occur. In the first instance, the 1,4 naphthoquinone reacts with the alkoxy furan, the product tautomerizes in the presence of a base to hereinbefore described first synthesis intermediate whose formula has been shown. And, when conventional Williamson-ether synthesis alkylating agents such as dimethyl sulfate in boiling acetone are added in the presence of base, methylation occurs at the phenolic positions to provide methyl protecting or blocking groups, and the second synthesis intermediate herein described.

In actual practice, the addition reaction, the tautomerization and the addition of the protecting alkylating groups such as methyl groups, all occur in the same reaction vessel, as will be apparent from the examples hereinbelow. It is for this reason that although three different chemical reaction steps occur, each of these have been described as forming a part of the first reaction step of the synthesis.

The product of this first reaction step, whose formula has previously been given, for purposes of succinctness, is described as the second synthesis intermediate. It is a bright red oil and may be easily separated by filtering from the solvent and other reactants of the first step.

This second synthesis intermediate is then hydride reduced to reduce the functional groups of the two position moiety, that is, "A" to alcoholic functional groups. It has heretofore been mentioned that "A" may be a keto group, an ester group, an aldehyde group, or a nitrile group. These are now hydride reduced so that whatever functional groups are represented by "A", are reduced to a hydroxyl containing moiety. This reduction is necessary so that cyclization may occur in a reaction step which is described hereinafter.

Hydride reduction is well known. Suitable reducing agents which may be employed are sodium borohydride and lithium aluminum hydride. If "A" represents an ester moiety, lithium aluminum hydride must be employed as the reducing agent. In fact, lithium aluminum hydride is the preferred reducing agent for all of the hydride reductions which occur.

In the hydride reduction step, the reducing agent, such as lithium aluminum hydride, in ether, again under anhydrous conditions, is added to the heretofore described bright red oil synthesis intermediate, in order to reduce the "A" substituent to an alcoholic moiety. Again, it is preferred that equal molar amounts be employed. As is well known, the reaction must be anhydrous to prevent reaction between the water and the hydride reducing agent. Pressure is not a factor. While it is preferred that ether be employed as the solvent, other solvents such as tetrahydrofuran or glyme may be employed. The reaction may be run at temperatures from −78° C. up to 0° C., or even higher to room temperature. The product of this reaction, assuming that "A" represents an acetyl group, may be represented by the following structural formula:

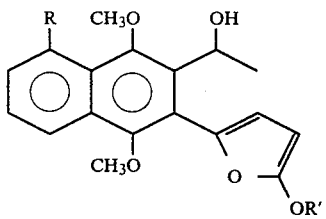

This second synthesis intermediate, with the reduced alcoholic group, is a pale yellow oil and filtration and evaporation of the solvent may be used for separation of the same.

After separation of this pale yellow oil intermediate, the next step of the process involves removal of the alkyl portion of the alkoxy furan with a deblocking agent and internal cyclization in order to provide ring formation between the two position alcoholic moiety of the naphthoquinone ring structure and the alkoxyfuran.

These functions are accomplished by use of a deblocking agent and an internal cyclization agent. The terms "deblocking agent" and "cyclization agent" are well known to organic synthesis chemists, and readily understood. They define the function of the chemical employed. For further details see Reagents for Organic Synthesis, Fieser and Fieser, Vols. 1–6, which is incorporated herein by reference. While the precise agents mentioned hereinafter are preferred, others performing the same function can also be employed.

The preferred deblocking agent is trifluoroacetic acid in methylene chloride but others such as paratolulene sulfonic acid or naphthalene sulfonic acid may be equally satisfactorily employed.

The preferred internal cyclization agent is diaza bicyclononane, however others such as triethylamine, diazabicycloundecane or diazabicyclooctane can be employed. The common factor being with these cyclization agents that they are all Lewis bases and might be termed non-nucleophilic bases.

With respect to this reaction wherein the ring formation by internal cyclization occurs as well as along with deblocking of the alkoxy group, anhydrous conditions must be employed and the reaction must be conducted in a solvent such as chloroform, toluene or ether. Temperature does not appear to be an important reaction factor.

The reaction product, again assuming that "A" represented an acetoxy group, can be represented by the following formula:

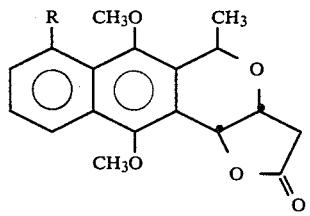

In the final step of the reaction process, oxidative dealkylation to remove the blocking CH₃ groups is employed. One oxidative dealkylation which can be employed is known as a Rapoport's procedure. For details of such a procedure, see C. D. Snyder and H. Rapoport, *Journal American Chemical Society*, Vol. 94, page 227 (1972) which is incorporated herein by reference. In this reaction, silver oxide in the presence of nitric acid may be employed for oxidative demethylation. However, a suitable alternative is nitric acid in acetic acid. Since the Rapoport oxidative demethylzation procedure is known and described in the incorporated by reference Journal article, details will not be given herein, except in the specific working examples.

In the final reaction step, the CH₃O groups are reconverted to diones, and assuming that in the initial reaction step "R" equals hydrogen, "A" equals CH₃CO, the product of the reaction would be deoxykalafungin, which has the following formula:

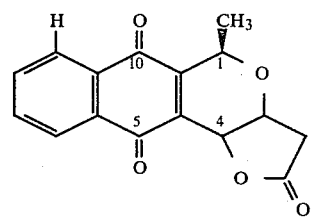

If the "R" hydrogen moiety as shown was replaced with an OH group, the product is kalafungin.

In repeating several different runs of the reaction, an overall reaction yield as measured from starting materials to the final deoxykalafungin product, has been as high as 17%. This yield for complex syntheses as shown herein is considered extremely good.

The following examples are shown to further illustrate, but not limit, the process of this invention.

EXAMPLES

The following general information should be noted. Diethyl ether and tetrahydrofuran were distilled from lithium aluminum hydride. All organic extracts were dried over Na₂SO₄. Melting points were determined on a Fisher-Johns melting point apparatus and are uncorrected. Infrared spectra were determined on a Beckman IR-4250 spectrometer. Nuclear magnetic resonance spectra were determined on a Varian EM-360 instrument in CDCl₃ with absorptions recorded in ppm downfield from internal Me₄Si. Ultraviolet spectra were recorded using a Cary Model 14 spectrometer. High resolution mass spectra were recorded on an AEI MS-902 high-resolution mass spectrometer. Elemental ayalyses were performed by Galbraith Laboratories, Inc.

To a 1.0 M toluene solution of 2-acetyl-1,4-naphthoquinone (340 mg. 1.7 mmol) at $-78°$ C. under nitrogen was added via syringe a 1.0 M toluene solution of 2-tertbutoxyfuran (250 mg. 1.8 mmol). The resoluting solution was allowed to warm slowly to room temperature. The solvent was removed under reduced pressure and replaced with 15 mL of anhydrous acetone. Potassium carbonate (730 mg, 5.3 mmol) and dimethyl sulfate (500 mg, 4.0 mmol) were added, and the solution was heated at reflux for 8 hours. The cooled solution was filtered and the filtrate was concentrated. Silica gel chromatology (10:1 hexane-ether) yielded 390 mg (62%) of a bright red oil: IR (film) 1610, 1387, 1145 cm; NMR (CDCl₃) 1.42 (s, 9H), 2.53 (x, 3H), 3.80 (s, 3H), 3.94 (s, 3 H), 5.63 (d, 1H, J=3 Hz), 6.85 (d, 1 H, J=3 Hz), 7.56 (m, 2H), 8.15 (m, 2 H). High-resolution mass spectrum for $C_{22}H_{24}O_5$ required m/e 368.16238; found m/e 368.16171.

To a stirred solution of lithium aluminum hydride (20 mg, 0.50 mmol) in ether (1.0 mL) at $-10°$ C. under $N_2$ was added the red oil, 1,4-dimethoxy-2-acetyl-3-(5-tert-butoxy-2-furyl) naphthalene, (390 mg. 1.06 mmol) in (1.0 mL of ether. The solution was stirred for 30 minutes at $-10°$ C. and then quenched by slow addition of 5 drops of water, 5 drops of 1 N NaOH, and then 1 mL of $H_2O$. After stirring for a further five minutes, the solution was filtered, diluted with ether, and dried. Filtration and evaporation of the solvent yielded 350 mg (96%) of a pale yellow oil; IR (film) 3450, 2980, 2850, 775 cm; NMR ($CDCl_3$) 1.41 (s, 9 H), 1.56 (d, 3 H, J=7 Hz), 3.67 (s, 3 H), 4.06 (s, 3 H), 4.18 (br s, 1H) 4.35 (q, 1H, J=7 Hz), 5.64 (d, 1 H, J=3 Hz), 6.43 (d, 1H, J=3 Hz), 7.52 (m, 2H), 8.13 (m, 2H). High resolution mass spectrum for $C_{22}H_{26}O_5$ required m/e 370.17803; found m/e 370.17909.

To a 0.5 M methylene chloride solution of the pale yellow oil, 1,4-dimethoxy-2-(d-hydroxyethyl)-3-(5-tert-butoxy-2-furyl)-napthalene (310 mg, 0.84 mmol) at 0° C. under $N_2$ was added 1 equivalent of trifluoroacetic acid deblocking agent. The ice bath was removed and the solution stirred for 30 minutes. Benzene was added (5 mL), and the solvents were removed at reduced pressure (repeated three times). The material remaining was dissolved in 4 mL of dry benzene, and 1 equivalent of diazabicyclononane cyclization agent was added. After stirring for 30 minutes at room temperature, the solution was diluted with 20 mL of 1:1 benzene-ether and washed with 5 mL of 0.5 M HCl and then brine. The organic layer was dried and filtered, and the solvent was removed at reduced pressure. Silica gel chromatography (hexane-EtOAc) yielded 90 mg (35%) synthesis intermediate, as colorless crystals. NMR data showed this material to be a 3:1 mixture of epimers about C-1:IR (major) 1780 cm; NMR ($CDCl_3$) (major) 1.50 (d, 3H, J=7 Hz), 2.57 (d, 1H, J=18 Hz), 3.02 (dd, 1 H, J=18.45 Hz), 3.93 (s, 3H), 4.08 (s, 3H), 4.72 (dt, 1H, J=4.5, 3.0 Hz), 5.37 (q, 1H, J=7 Hz), 5.58 (d, 1H, J=3 Hz), 7.54 (m, 2H), 8.05 (m, 2H), Anal. Calcd. for $C_{18}H_{18}O_5$; C, 68.78, H, 5.77. Found: C, 68.57; H, 5.79.

To the synthesis intermediate having the blocked methyl groups, whose formula is shown in the specification at page 10, (68 mg, 0.216 mmol) and argenic oxide (110 mg, 0.9 mmol) in 2.0 mL of THF was added 0.2 mL of 6 N $HNO_3$. This is Rapoport's Procedure of oxidative demethylation. After this disappearance of the argenic oxide (approximately 5 minutes), the reaction was terminated by addition of 10 mL of 4:1 $CHCl_3—H_2O$ The mixture was diluted with $CHCl_3$ and washed twice with water and once with brine. The organic layer was dried and filtered, and the solvent was removed in reduced pressure. Recrystallization from ether yielded 58 mg (95%) of orange crystals; mp 181°-183° C.; IR (Nujol) 1780, 1660 cm; NMR ($CDCl_3$) 1.56 (d, 3H, J=7 Hz), 2.65 (d, 1H, J=18 Hz), 3.10 (dd, 1 H, J=18, 4.5 Hz), 4.78 (dt, 1H, J=4.5,3 Hz), 5.13 (q, 1H, J=7 Hz), 5.39 (d, 1H, J=3 Hz), 7.87 (m, 2H), 8.22 (m, 2H); UV ($CHCl_3$), 241, 248, 255, 267 sh, 345 nm, Anal. Calcd for $C_{16}H_{12}O_5$; C, 67.40; H, 4.26, Found: C, 67.40; H, 4.34.

The overall yield of 9-deoxykalafungin was 17%.

Similar reactions have been conducted wherein R equals $OCH_3$ and the naturally occurring product kalafungin prepared. Additionally, similar product has been prepared for R is an acetoxy group.

Reaction has also been run where R' is tertiarybutyldimethylsiloxy.

As heretofore mentioned, the 9-deoxykalafungin prepared in accordance with the process of this invention is a novel compound. A comparison of its inhibitory effects on certain micro-organisms and fungi, with the known compound kalafungin is enclosed.

| Test Organisms | | Minimum Inhibitory Concentration (ug/ml) | |
|---|---|---|---|
| | | Kalafungin | Deoxy-kalafungin |
| *Nocardia asteroides* | UC 2052 | 3.9 | 3.9 |
| *Blastomyces dermatitidis* | UC 1466 | ≦1.0 | ≦1.0 |
| *Geotrichum sp.* | UC 1207 | 3.9 | 3.9 |
| *Hormodendrum compactum* | UC 1222 | 3.9 | 2.0 |
| *Phialophora verrucosa* | UC 1807 | ≦1.0 | ≦0.5 |
| *Cryptococcus neoformans* | UC 4869 | 2.0 | 2.0 |
| *Cryptococcus neoformans* | UC 1139 | ≧1.0 | 1.0 |
| *Sporotrichum schenckii* | UC 1364 | 15.6 | 7.8 |
| *Monosporium apiospermum* | UC 1248 | ≦1.0 | 1.0 |
| *Candida albicans* | UC 7163 | 7.8 | 7.8 |
| *Candida albicans* | UC 7164 | 7.8 | 15.6 |
| *Microsporum canis* | UC 1395 | 7.8 | 7.8 |
| *Trichophyton rubrum* | UC 1458 | ≦1.0 | ≦0.5 |
| *Trichophyton violaceum* | UC 1459 | 2.0 | ≦0.5 |
| *Trichophyton asteroides* | UC 4775 | 2.0 | 1.0 |
| *Trichophyton mentagrophytes* | UC 4797 | 3.9 | 2.0 |
| *Trichophyton mentagrophytes* | UC 4860 | 2.0 | 1.0 |

It can therefore be seen that deoxykalafungin is a potent inhibitor of a wide variety of pathogenic fungi. Indeed, in many instances, it has greater minimum inhibitory concentrations than does kalafungin.

What is claimed is:

1. A method of preparing quinone pyrano-gamma-lactones, said method comprising,
    reacting, under anhydrous conditions, a two position functionally substituted 1,4 naphthoquinone with a two substituted acid labile alkoxy furan, said two position functionally substituted moiety of said 1,4 naphthoquinone being one which can be reduced to an alcoholic functional group to provide a first synthesis intermediate,
    adding an acid stable alkylating agent in the presence of a base to said first synthesis intermediate to alkylate and protect the 1,4 position keto groups of said naphthoquinone,
    reducing with a hydride the functional groups of said two position functionally substituted moiety to provide a second synthesis intermediate having alcoholic functional groups at said two position,
    treating said second synthesis intermediate with a deblocking agent to remove the alkyl group from the alkoxy furan and thereafter treating with a Lewis base an internal cyclization agent to provide ring formation between said alcoholic functional group and said furan ring, and
    thereafter, oxidatively dealkylating said 1,4 positions to provide a quinone pyrano-gamma-lactone.

2. The method of claim 1 wherein said two position functionally substituted moiety is selected from the group consisting of keto substituents, ester substituents, aldehyde substituents and nitrile substituents.

3. The method of claim 2 wherein said alkoxy furan is selected from the group consisting of 2-tert-butoxy furan and 2-(tert-butyldimethylsiloxy) furan.

4. The process of claim 1 wherein said alkylating agent is dimethyl sulfate.

5. The method of claim 4 wherein said dimethyl sulfate alkylating agent is added in the presence of boiling acetone.

6. The process of claim 1 wherein said reduction of said two position substituted moiety to an alcoholic functional group is with a reducing agent selected from the group consisting of lithium aluminum hydride, and sodium borohydride.

7. The method of claim 1 wherein said deblocking agent is trifluroacetic acid in the presence of methylene chloride.

8. The process of claim 7 wherein said internal cyclization agent comprises at least an equivalent amount of an agent selected from the group consisting of diazabicyclononane, triethylamine, diazabicycloundecane and diazabicyclooctane.

9. The method of claim 1 wherein said oxidative dealkylating of said 1,4 positions is by use of Rapoport's procedure.

10. The method of claim 1 wherein said oxidative dealkylating agent is nitric acid in an acetic acid solvent.

* * * * *